United States Patent
Ogawa

Patent Number: 6,159,206
Date of Patent: Dec. 12, 2000

[54] MEDICAL IMPLEMENT FOR DEPOSITING IMPLANTED DEVICE AND METHOD OF DEPOSITING IMPLANTED DEVICE

[75] Inventor: Atsushi Ogawa, Kanagawa, Japan

[73] Assignee: Kaneka Medix Corporation, Osaka, Japan

[21] Appl. No.: 09/331,269

[22] PCT Filed: Oct. 29, 1998

[86] PCT No.: PCT/JP98/04894

§ 371 Date: Jun. 17, 1999

§ 102(e) Date: Jun. 17, 1999

[87] PCT Pub. No.: WO99/22651

PCT Pub. Date: May 14, 1999

[30] Foreign Application Priority Data

Oct. 30, 1997 [JP] Japan ................................. 9-298889

[51] Int. Cl.[7] .................................................. A61B 17/38
[52] U.S. Cl. .................................................. 606/32; 606/29
[58] Field of Search .............................. 606/27, 28, 29, 606/32; 600/585

[56] References Cited

U.S. PATENT DOCUMENTS

| | | |
|---|---|---|
| 5,122,136 | 6/1992 | Guglielmi et al. . |
| 5,354,295 | 10/1994 | Guglielmi et al. ..................... 606/32 |
| 5,522,836 | 6/1996 | Palermo . |
| 5,540,680 | 7/1996 | Guglielmi et al. ..................... 606/32 |
| 5,569,245 | 10/1996 | Guglielmi et al. ..................... 606/49 |
| 5,624,449 | 4/1997 | Pham et al. ......................... 606/108 |
| 5,743,905 | 4/1998 | Eder et al. ........................... 606/32 |
| 5,759,161 | 6/1998 | Ogawa et al. . |
| 5,851,206 | 12/1998 | Guglielmi et al. ..................... 606/28 |
| 5,855,578 | 1/1999 | Guglielmi et al. ..................... 606/32 |
| 5,947,962 | 9/1999 | Guglielmi et al. ..................... 606/32 |
| 5,947,963 | 9/1999 | Guglielmi ............................ 606/32 |
| 5,976,126 | 1/2000 | Guglielmi ............................ 606/32 |
| 5,976,131 | 11/1999 | Guglielmi ............................ 606/49 |
| 6,010,498 | 1/2000 | Guglielmi ............................ 606/32 |

FOREIGN PATENT DOCUMENTS

| | | |
|---|---|---|
| 5-500322 | 1/1993 | Japan . |
| 7-503165 | 4/1995 | Japan . |
| 7-265431 | 10/1995 | Japan . |
| 8-509901 | 10/1996 | Japan . |
| 11-47138 | 2/1999 | Japan . |

*Primary Examiner*—Paul J. Hirsch
*Assistant Examiner*—Michael B. Priddy
*Attorney, Agent, or Firm*—Frishauf, Holtz, Goodman, Langer & Chick, P.C.

[57] ABSTRACT

Disclosed herein are a medical implement and a method, by which the length or volume of an implanted device actually deposited can be changed or adjusted even after inserted into a patient's body, and thus an implanted device of an appropriate length or volume can be deposited. The medical implement for depositing an implanted device comprises a catheter which is to be inserted into a patient's body and has an electrode at its distal part, and a wire device guided by the catheter. The wire device comprises a wire and the implanted device connected to the distal end of the wire through a first severable joint member. The implanted device has a structure that a plurality of implanted elements are joined to each other through one or more second severable joint members, successively. The first joint member or any one of the second joint members is severed in a state that the implanted device is projected from the distal end of the catheter.

12 Claims, 4 Drawing Sheets

MEDICAL IMPLEMENT FOR DEPOSITING IMPLANTED DEVICE AND METHOD OF DEPOSITING IMPLANTED DEVICE

TECHNICAL FIELD

The present invention relates to a medical implement for depositing a necessary implanted device at an intended site in a patient's body through a tubular organ thereof, and a method of depositing an implanted device using this medical implement.

BACKGROUND ART

Various problems are generally presented in treatment involving surgery to a patient's body. For example, the patient undergoing an operation must withstand the long hours of stress of the procedure. The surgeon, as well, is forced to endure intense concentration for the long period of operation. The danger of infection is always a possibility.

In order to lighten such various stress and to perform a necessary operation more safely and easily, various medical instruments such as catheters, guide wires and embolizing materials for occluding tubular organs such as vessels have recently been developed and been put to practical use.

With the recent advancement in medical instruments such as catheters and guide wires, an endovascular operation in which the intended diseased part is approached through a vessel is currently often performed in the treatment of diseases such as arteriovenous malformation, cerebral aneurysm and carotid-cavernous fistula.

At present time, releasable balloons, coils, liquid embolizing substances, particulate embolizing substances and the like are used as tubular organ embolizing materials. Once such an embolizing material is left or released at an erroneous or undesirable site in a tubular organ, however, it is generally next to impossible to recover it or to change the site.

Under such circumstances, proposals have heretofore been made for releasable embolizing materials, by which an embolizing material can be pulled back and reinserted even when one fails to deposit it at the intended site, and can be released and left after confirmation of the deposited site.

For example, Japanese Patent Application Laid-Open No. 500322/1993 (though PCT route) and Japanese Patent Application Laid-Open No. 265431/1995 proposed a method of leaving an embolizing material in, for example, an aneurysm, wherein the embolizing material such as a coil is provided at a distal end of a guide wire with a proper severable joint member, the embolizing material is placed at the intended site, and the joint member is then severed, thereby detaching the embolizing material from the guide wire to deposit it.

In order to detach the embolizing material in such a method, there is utilized a means of forming the joint member with a stainless steel and electrolyzing it by a positive current, thereby dissolving it, or a means of forming the joint member with polyvinyl alcohol and melting and severing it with a high-frequency current.

When an embolizing material is deposited at an affected part such as an aneurysm, it is generally conducted to first insert a microcatheter into the aneurysm and then send the embolizing material such as a coil by means of a wire for deposition through the microcatheter, thereby filling the embolizing material into the aneurysm. Two or more embolizing materials are successively inserted and deposited unless the aneurysm is fully filled with one embolizing material.

In the conventional medical implements for depositing implanted devices, however, embolizing materials to be inserted are those of specified lengths selected by expecting from various conditions. Therefore, in some cases, an embolizing material may actually not be completely inserted into an aneurysm since the aneurysm is filled up at a stage that the embolizing material is inserted halfway. In this case, it must be absolutely avoided to force the remainder of the embolizing material to insert into the aneurysm, since the cause of aneurysmal rupture is formed. On the other hand, when the remainder of the embolizing material is left in a vessel (parenteral artery) outside the aneurysm, the cause of thrombosis is formed. Therefore, it is necessary to pull back such an embolizing material to change it to an embolizing material of a proper length and to deposit the new embolizing material again.

However, when the embolizing material inserted halfway once is pulled back, the embolizing material may be entangled with an embolizing material already placed, or the coiled form of the embolizing material may be deformed. Further, both insertion and pulling out thereof may become impossible in some cases.

SUMMARY OF THE INVENTION

As described above, the conventional medical implements for depositing an implanted device involve a problem that the length or volume of the implanted device to be deposited at an intended site in a patient's body cannot be changed after insertion thereof, and so a desired deposition of an implanted device cannot be carried out with ease.

It is an object of the present invention to solve such a problem and to provide a medical implement for depositing an implanted device, comprising a wire device for depositing an implanted device, which is capable of changing or adjusting the length or volume of an implanted device actually deposited even after inserted into a patient's body and thus easily leaving and depositing an implanted device of an extremely appropriate length or volume, and a catheter for guiding the wire device for depositing the implanted device, wherein a severing operation can be performed through the catheter, and a method of depositing an implanted device using this medical implement.

According to the present invention, there is provided a medical implement for depositing an implanted device, comprising a catheter which is to be inserted into a patient's body and which has an electrode at a distal part of the catheter, and a wire device for depositing the implanted device, which is guided by the catheter, wherein the wire device comprises a wire for depositing the implanted device, and the implanted device being connected to the distal end of the wire through a first severable joint member, said implanted device having a structure such that a plurality of implanted elements are joined to each other through one or more second severable joint members successively, and wherein the first joint member or any one of the second joint members of the wire device is severed by supplying the electrode of the catheter with electric power in a state such that the implanted device of the wire device guided through the catheter is projected from the distal end of the catheter;

In this medical implement, it may be preferred that the first joint member or any one of the second joint members be melted and severed at the distal end of the catheter by applying a high-frequency current to the electrode of the catheter.

The implanted elements of the implanted device may be formed by a biocompatible metallic coil.

The first joint member and the second joint members may be formed by a material capable of being melted and severed by heat, for example, a polyvinyl alcohol type polymer.

It may be preferred that a leading implanted element among the plural implanted elements making up the implanted device be the longest. The first joint member and the second joint member or plural second joint members may be formed by an integral common joint member.

The implanted elements may be provided with a fibrous material for promoting the formation of thrombus, or may have a shape-memory property.

According to the present invention, there is also provided a method of depositing an implanted device, which comprises the steps of:

inserting a catheter having an electrode at its distal part into a patient's body to locate the distal end thereof at a site intended to deposit the implanted device; and guiding a wire device for depositing the implanted device, which wire device comprises a wire for depositing the implanted device, and the implanted device being connected to the distal end of the wire through the a first severable joint member, said implanted device having a structure such that a plurality of implanted elements are joined to each other through one or more second severable joint members successively, through the catheter to sever the first joint member or any one of the second joint members of the wire device by supplying the electrode of the catheter with electric power in a state such that the implanted device is projected from the distal end of the catheter, whereby the whole or a part of the implanted elements is deposited at the intended site.

In this method, it may be preferred that the step of severing the first joint member or any one of the second joint members be conducted by applying a monopolar high-frequency current between the electrode of the catheter and a counter electrode for body earth ground provided on the skin surface of the patient's body.

According to the medical implement having such a construction as described above, the wire device for depositing the implanted device is inserted into the patient's body through the catheter, whereby the implanted device is deposited at the intended site such as an aneurysm. Although the implanted device is connected to the wire through the first joint member, and the plural implanted elements making up the implanted device are joined to each other through one or more second joint members, all of these joint members are severable by supplying the electrode of the catheter with electric power, and so the length or volume of an implanted device actually separated and deposited can be changed or adjusted by selecting a joint member to be severed. Therefore, an implanted device of an appropriate length or volume can be deposited at the intended site with extreme ease.

[Description of characters]
- 10 Wire device
- 12 Wire for deposition
- 12A Proximal part
- 12B Tapered part
- 13 Coiled member for connection
- 13A Small-diameter part
- 13B Large-diameter part
- 15 First joint member
- 16 Composite coil
- 16A to 16D Coil elements
- 17A to 17C Second joint members
- 18 Semi-spherical part
- 20 Adhesive joint
- 25 Common joint member
- 28 Fibrous material
- 30 Microcatheter
- 31 Catheter body
- 32 Proximal operating part
- 33 Braid
- 34 Metallic lead wire
- 35 Electrode
- 38 High-frequency power source

BEST MODE FOR CARRYING OUT THE INVENTION

The embodiments of the present invention will hereinafter be described with reference to the drawings.

Figure 1:
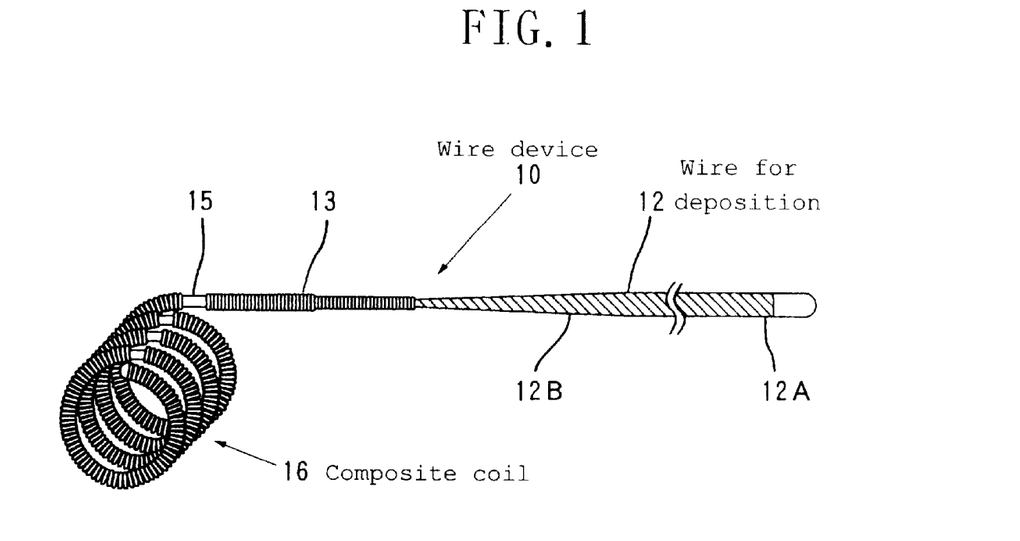
FIG. 1 is an explanatory perspective view illustrating the overall construction of a wire device in an embodiment of the medical implement for depositing an implanted device according to the present invention.
Figure 2:
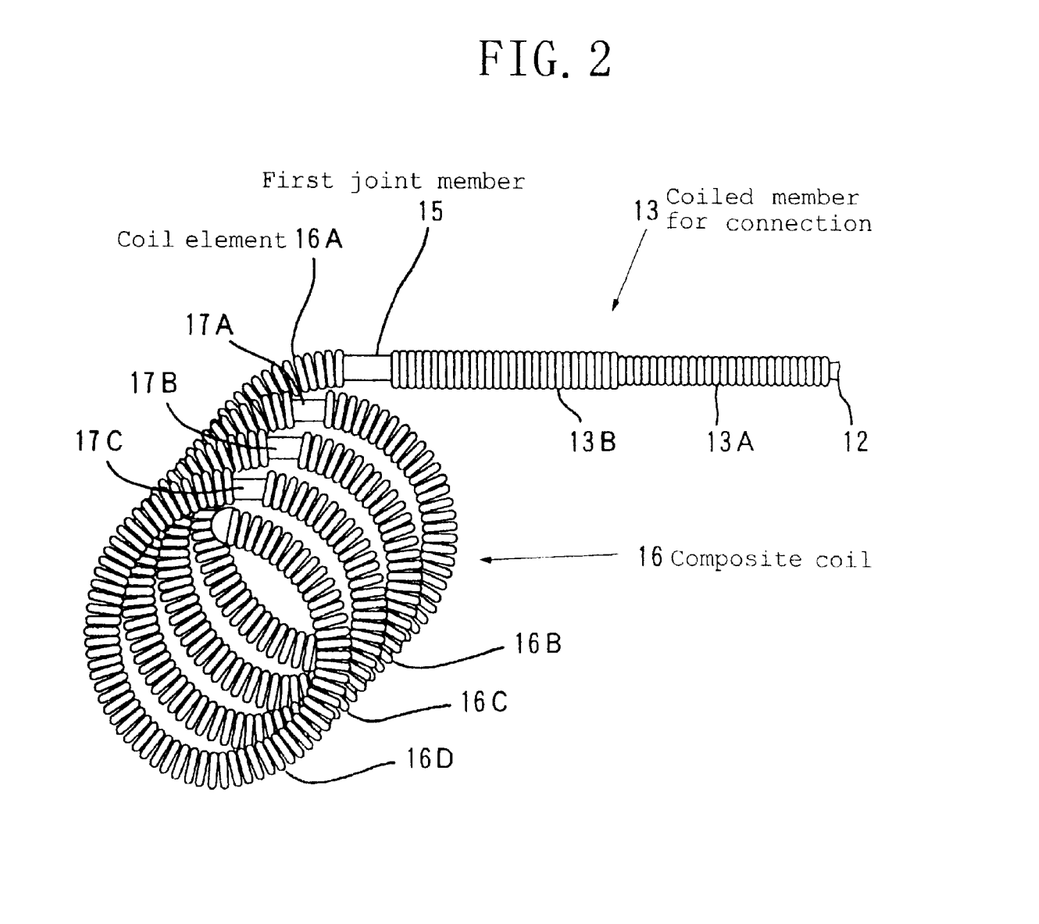
FIG. 2 is an enlarged view illustrating a composite coil constituting the implanted device shown in FIG. 1 and a joined state therein.
Figure 3:
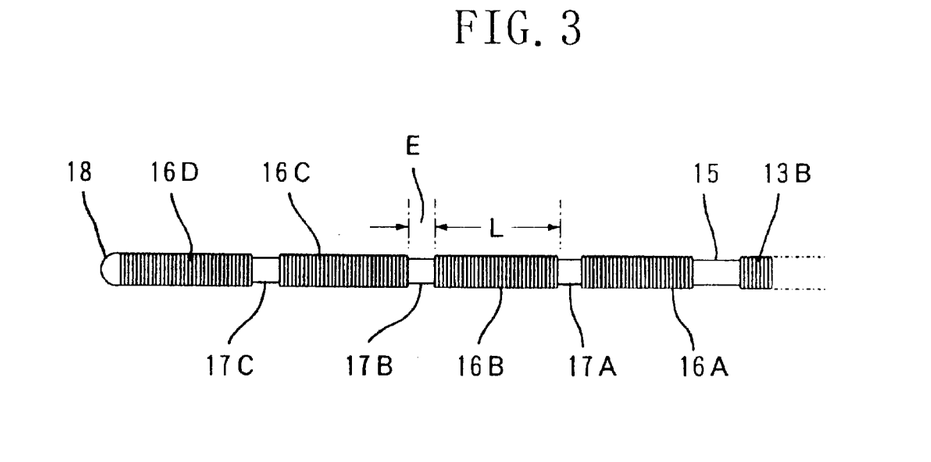
FIG. 3 is an explanatory view illustrating the composite coil of FIG. 2 in an elongated state.
Figure 4:
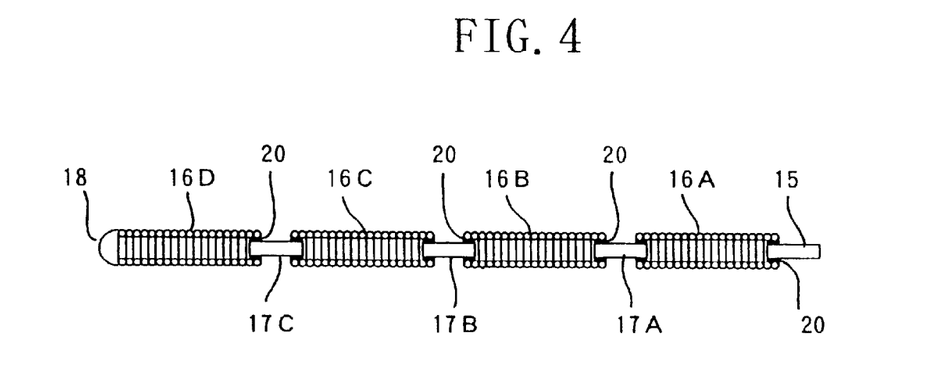
FIG. 4 is an explanatory sectional view of the composite coil shown in FIG. 3.

FIG. 1 is an explanatory perspective view illustrating the overall construction of a wire device in an embodiment of the medical implement for depositing an implanted device according to the present invention, FIG. 2 is an enlarged view illustrating a composite coil constituting the implanted device shown in FIG. 1 and a joined state therein, FIG. 3 is an explanatory view illustrating the composite coil of FIG. 2 in an elongated state, and FIG. 4 is an explanatory sectional view of the composite coil body shown in FIG. 3.

The wire device 10 is elementally composed of a wire 12 for deposition, which is used as a pusher, a coiled member 13 for connection, the first joint member 15 and a composite coil 16 constituting an implanted device.

The wire 12 for deposition is formed of, for example, a stainless steel and comprises a proximal part 12A shown on the right-hand side in FIG. 1 and a flexible tapered part 12B the outer diameter of which gradually decreases toward the distal end (the left-hand side in FIG. 1) thereof. On the distal part of the tapered part 12B, is fitted a proximal part of a small-diameter part 13A of the coiled member 13 for connection made of, for example, a stainless steel and having the small-diameter part 13A and a large-diameter part 13B.

The wire 12 for deposition is constructed by, for example, closely winding a winding wire in a coiled state on the peripheral surface of a core wire. The outer diameter of the wire 12 is preferably 0.1 to 2.0 mm, and its length is variously selected according to the purpose and is within a range of, for example, 100 to 2,000 mm.

A proximal part of the first joint member 15 in the form of a short rod, which is comprised of a polyvinyl alcohol type polymer, is fitted into a distal part of the large-diameter part 13B of the coiled member 13 for connection and bonded and fixed thereto with an adhesive. A distal part of the first joint member 15 is fitted into a proximal part of the first coil element 16A of the composite coil 16 and bonded and fixed thereto with an adhesive, whereby the wire 12 is integrally connected to the composite coil 16 through the first joint member 15.

The composite coil 16 constituting an implanted device comprises a plural coil elements (4 elements in the illustrated embodiment) 16A to 16D connected in series to one another in that order through a total of 3 second joint members 17A to 17C in the form of a short rod, which are composed of a polyvinyl alcohol type polymer. Specifically, two of the coil elements are connected by fitting both ends of the second joint member into ends of corresponding coil elements to be connected and bonding and fixing them to each other with an adhesive as illustrated in FIG. 4. Reference numeral 18 indicates a semi-spherical part formed at an end of the leading coil element 16D and having a smooth surface. This part 18 is formed by, for example, heating and melting a wire material of the coil element. Reference numeral 20 designates an adhesive joint.

The coil elements 16A to 16D making up the composite coil 16 are each formed by a biocompatible metallic coil. A specific material used for the coil elements 16A to 16D is selected from among platinum, tungsten, tantalum, gold, palladium, rhodium, titanium and alloys thereof, with platinum or an alloy of platinum and tungsten being particularly preferred. The coil elements comprised of such a material are X-ray impervious and thus can be visually observed by radiography.

The illustrated coil elements 16A to 16D are each in a double-coiled form as its original form, and its length L in a state of a primary coil (see FIG. 3) corresponds to about 1 turn of the double coil in FIG. 1, to which, however, the invention is not limited.

The second joint members 17A to 17C making up the composite coil 16 are each formed by the same material as that used in the first joint member 15, and the lengths and forms thereof may be the same as one another. Each of these joint members has a proper length so that a part of the peripheral surface is exposed in the connected state.

The dimensional ranges of the composite coil 16 may be exemplified as follows:
Diameter of a wire material for each of the coil elements 16A to 16D:
0.01 to 0.1 mm;
Outer diameter of the primary coil:
0.1 to 1.0 mm; and
Outer diameter of the secondary coil:
1.0 to 20.0 mm.

The outer diameter of each of the first joint member 15 and the second joint members 17A to 17C is determined to be a size fitted for the inner diameter of the primary coil of the corresponding coil element, and its length may be optional so far as it is sufficient for connection. However, it is preferred that the length E of the exposed part thereof be 0.5 to 2.0 mm.

No particular limitation is imposed on the material for the joint members (including all of the first joint member 15 and the second joint members 17A to 17C) so far as it does not adversely affect a patient's body and can be optionally severed after inserted into the patient's body. However, it is preferred that the material can be severed by applying a current to an electrode provided in a microcatheter, which will be described subsequently, or by heating. A material capable of being melted and severed by heating with a high-frequency current, for example, a polyvinyl alcohol type polymer is particularly preferred.

No particular limitation is imposed on the form of the connection with the joint members. For example, adhesive bonding, welding, connection by physical force or any other means may be utilized. Of these, the adhesive bonding is particularly preferred. In this case, for example, a cyanoacrylate type adhesive may be preferably used as the adhesive.

In the above-described wire device, the number of coil elements, the length and form of each coil element, and the like may be freely determined without any particular limitation. The composite coil may comprise by connecting coil elements different in length and form from one another. In the case where coil elements different in length are connected, they may be connected in such a manner that a coil element (17A) connected through the first joint member 15 is the shortest, a leading coil element is the longest, and intermediate coil elements become gradually longer successively. Such a construction has the advantage of affording the resulting wire device a wide freedom of actual use, since the length of an implanted element inserted and placed later becomes gradually shorter.

Figure 5:
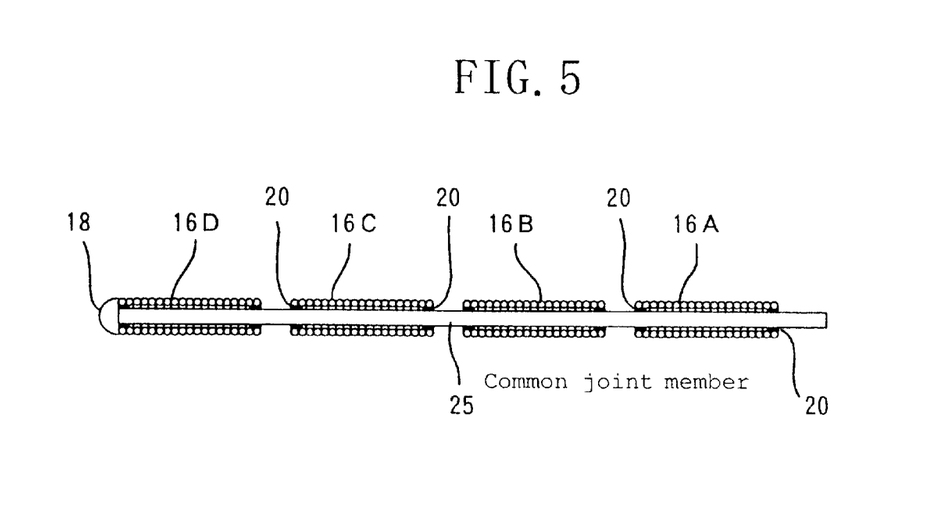
FIG. 5 is an explanatory sectional view illustrating a composite coil according to another embodiment.

FIG. 5 is an explanatory sectional view illustrating a composite coil 16 according to another embodiment. In this embodiment, all of the first joint member 15 and the second joint members 17A to 17C in the embodiment illustrated in FIG. 3 are formed by a common joint member 25 comprising a rod.

Figure 6:
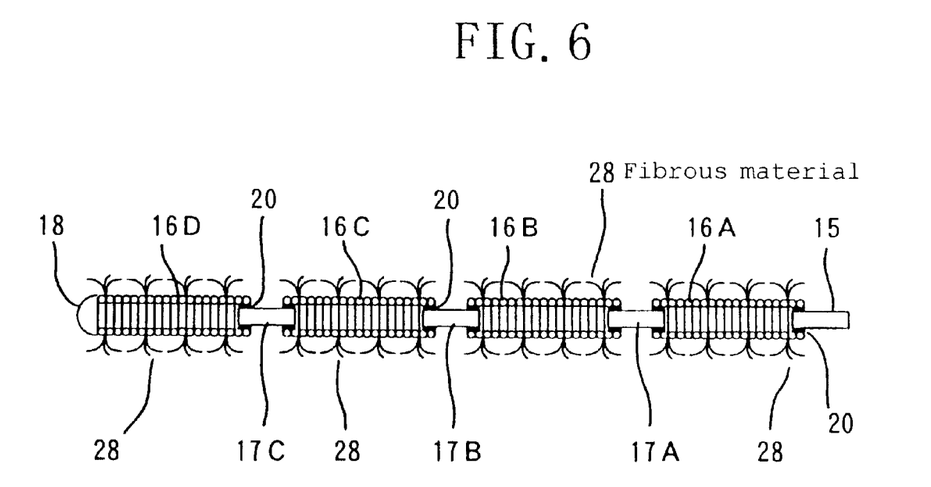
FIG. 6 is an explanatory sectional view illustrating a composite coil according to a further embodiment.

FIG. 6 is an explanatory sectional view illustrating a composite coil 16 according to a further embodiment. In this embodiment, the coil elements 16A to 16D in the embodiment illustrated in FIG. 3 are each provided with a fibrous material 28 capable of promoting the formation of thrombus in a state that it is projected radially outward with a length of about 1 to 10 mm. The fibrous material 28 comprises fibers of, for example, polyester, fluorocarbon resin, nylon or the like and can be provided by, for example, holding it between adjacent rings of a spiral wire constituting the primary coil in each of the coil elements 16A to 16D.

Figure 7:
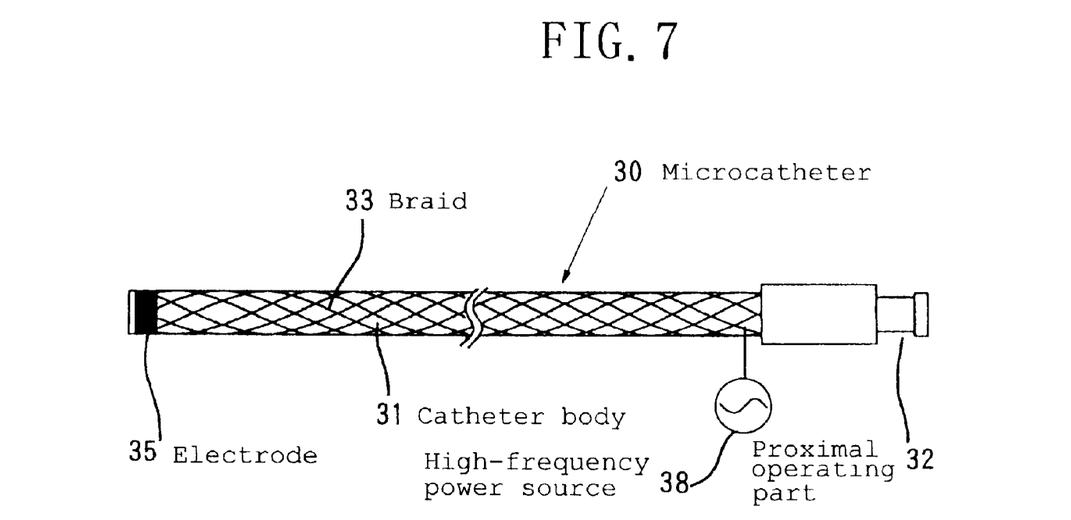
FIG. 7 is an explanatory front view illustrating the construction of a microcatheter used for inserting a wire into a patient's body.

The wire devices 10 described above are generally used together with a catheter. FIG. 7 is an explanatory front view illustrating the construction of a microcatheter advantageously used for inserting the wire device 10 described above into a patient's body. The microcatheter 30 according to this embodiment comprises a catheter body 31, a proximal operating part 32 provided on the proximal end of the catheter body 31, a braid 33 formed of a metallic braid, which is laid in the wall of the catheter body 31 and extends from the proximal end to the distal end of the catheter body, and a ring-shaped electrode 35 provided on the distal part of the catheter body 31. The electrode 35 is electrically connected to the braid 33. Reference numeral 38 indicates a high-frequency power source electrically connected to the braid 33 at the proximal part of the catheter body.

Figure 8:
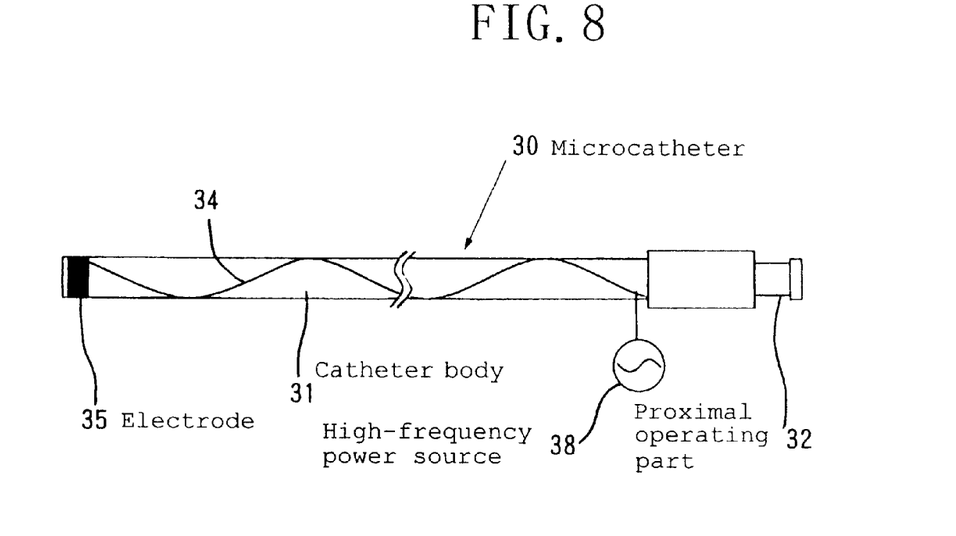
FIG. 8 is an explanatory sectional view illustrating a composite coil according to another embodiment.

FIG. 8 illustrates a microcatheter 30 similar to that shown in FIG. 7. In this embodiment, a metallic lead wire 34 extending from the proximal end to the distal end of a catheter body 31 is provided in place of the braid 33, and a high-frequency power source 38 and an electrode 35 are electrically connected to each other by this lead wire 34.

According to the medical implement for depositing an implanted device comprising such wire device 10 and microcatheter 30 as described above, an implanted device is deposited at the intended site in a patient's body in the following manner.

The microcatheter 30 is first inserted into the patient's body in accordance with a method known per se in the art, and its distal opening thereof is held in a state faced to a site intended to deposit the implanted device, for example, an open part of an aneurysm.

The wire device 10 is inserted into the microcatheter 30 through the proximal operating part 32 thereof with the composite coil 16 thereof in the lead, and pushed forward. At this time, the composite coil 16 moves along within the catheter body 31 in a state that the secondary coil of the coil elements 16A to 16D has been stretched in a substantially straight line along the catheter body 31.

When the coil elements 16A to 16D have a shape-memory property, it is also permissible to store the shape of the secondary coil in the coil elements 16A to 16D, then insert the wire device 10 into the catheter body 31 with the coil elements 16A to 16D stretched in a straight line (a state of a primary coil with a secondary coil uncoiled as illustrated in FIG. 3) and push it forward, and last return their shapes to the original forms.

The composite coil 16, which is an implanted device, is pushed by a necessary length out of the distal opening of the catheter body 31, and this projected portion of the composite coil is placed at an application site, for example, an aneurysm or the like. In the state that the composite coil portion of a necessary length or volume has been placed, a monopolar high-frequency current is applied between the electrode 35 provided on the distal part of the catheter body 31 and a counter electrode for body earth (ground) provided in advance on the skin surface of the patient's body by the high-frequency power source 38. The high-frequency current is applied to the electrode 35 through the braid 33 in the microcatheter 30 illustrated in FIG. 7 or the metallic lead wire 34 in the embodiment illustrated in FIG. 8.

In the operation described above, the state of the composite coil 16 projected from the microcatheter 30 can be known from radiography on the X-ray impervious coil elements with certain accuracy.

For example, when the electrode 35 is provided in a state exposed on the inner peripheral surface of the distal part of the catheter body 31 in such a manner that the coil elements 16A to 16D of the composite coil 16 in the wire device 10 move contacting with the electrode 35 when they pass through the electrode 35, what portion of the composite coil 16 is projected from the catheter body 31 can be detected with accuracy in the following manner. Namely, when the wire device 10 is inserted and pushed forward with the composite coil 16 in the lead while monitoring an electrical resistance value between a terminal provided on the catheter body 31 and a counter electrode provided on the patient's body, the electrical resistance value greatly lowers at the time the leading coil element 16D of the composite coil 16 is pushed out of the opening of the catheter body 31. Subsequently thereto, when the coil element 16D is separated away from the electrode 35, and the electrical insulating joint member 17C is situated at the opening of the catheter body 31, the electrical resistance value rises up. After this, such a change as the electrical resistance value lowers and then rises is repeated. Therefore, the state of such lowering or rise in electrical resistance value is monitored, whereby the projected portion can be known.

By applying the high-frequency current as described above, a joint member (in the illustrated embodiments, the first joint member 15 or any one of the second joint members 17A to 17C) nearest to the electrode 35 among those pushed out of the distal opening of the catheter body 31 is melted and severed by the heating action of the high-frequency current. As a result, the portion of the composite coil 16 beyond the severed joint member, i.e., a sole coil element or plural coil elements separated with their corresponding joint member(s) or residue thereof, are deposited as an actual implanted device.

In the composite coil 16 of the above-described wire devices 10, all of the first joint member 15 and the second joint members 17A to 17C are joint members severable by melting. Therefore, the length or volume of an implanted device actually deposited can be changed or adjusted with extreme ease by selecting a joint member to be severed. As a result, an implanted device of an extremely appropriate length or volume can be deposited with ease in a short period of time.

Specifically, it can be avoided with high reliability to deposit an implanted device of excess length or volume, so that there is next to no need to pull back the implanted device inserted once. Therefore, an accident or danger attendant on such an operation is also reduced to a great extent.

When the joint members are those comprised of a polyvinyl alcohol type polymer in the above-described wire devices, the joint members can be melted and severed by applying a high-frequency current for an extremely short period of within 1 to 3 seconds.

Although the present invention has been described specifically above, various changes may be made in the present invention. For example, the implanted devices are not limited to the composite coils, and any other suitable implanted devices of, for example, ring, pipe and capsule forms may be used. The joint members may be optional so far as they can join implanted elements to each other and can be optionally severed. The joint members may preferably be severed by applying a current utilizing an electrode provided on the distal end of a catheter which guides the wire device, from the practical point of view.

It is preferred that the joint member is severed by applying a monopolar high-frequency current, since the electrode 35 in the distal part of the catheter body can be comprised of a single electrode. However, a pair of electrodes may be provided with a gap therebetween on the distal part of the catheter body to apply a current through wire leads, thereby heating and severing the joint member at a position between both electrodes. In this case, it goes without saying that there is no need to provide a counter electrode on a patient's body.

The medical implements according to the present invention for depositing the implanted device will hereinafter be described by the following examples.

Production of wire device

Following the construction of FIG. 1, one end of the first joint member (15) comprised of a polyvinyl alcohol type copolymer in the form of a columnar rod having a diameter of 0.2 mm and a length of 10 mm was connected to a distal end of a wire (12) for deposition having a length of 1,800 mm and a diameter of 0.016 mm through a coiled member (13) for connection. On the other hand, the first coil element (16A) having a primary coil length of 30 mm and a secondary coil length of 10 mm formed by a platinum-tungsten alloy wire material having a diameter of 0.36 mm was connected to the other end of the first joint member in such a manner that the length (clearance E between the first coil element and the coiled member for connection) of an exposed part of the first joint member was 1 mm.

The same second joint member (17A) as the first joint member as above was used to connect the second coil element 16B to the first coil element in the same manner as in the connection by the first joint member. After this, the same process was repeated to produce a wire device (10) in which a composite coil (16) composed of 5 coil elements connected to one another through a total of 4 second joint members was connected to the wire for deposition through the first joint member.

In the above, a cyanoacrylate type adhesive was used for the connection between the joint member and the coiled member for connection or the coil element.

Production of microcatheter

A catheter body (31) having an inner diameter of 0.55 mm and an outer diameter of 0.95 mm, in the wall of which a braid (33) formed by arranging 8 stainless steel wires each having an outer diameter of 0.03 mm so as to extend spirally in a clockwise direction from one end to the other end of the catheter body and arranging the same 8 stainless steel wires as described above so as to extend spirally in a counter-clockwise direction was laid, was provided. On the inner peripheral surface of one end part of this catheter body, was provided a platinum ring having an outer diameter of 0.8 mm, an inner diameter of 0.6 mm and a width of 0.5 mm in an exposed state. This ring was electrically connected to the braid to provide an electrode (35), and a terminal electrically connected to the braid was provided on the other end part of the catheter body, thereby producing a microcatheter (30) equipped with an electrode.

Application Example

The medical implement for depositing an implanted device comprised of the wire device and microcatheter obtained in the above described manner was used to carry out an experiment on an embolizing treatment with an aneurysmal model formed in the carotid artery of an adult dog.

More specifically, the microcatheter was inserted into the femoral artery of the adult dog so as to reach the interior of the carotid artery, and the wire device was inserted into the microcatheter with the composite coil in the lead, and pushed forward. The pushing of the wire device was continued while monitoring an electrical resistance value between the electrode (35) of the catheter body (31) and a counter electrode attached to the back of the adult dog utilizing the fact that the every coil element of the composite coil (16) passes through while coming into contact with the electrode (35). As a result, lowering and rise in electrical resistance value were repeated. The reason for it is that such a change as the electrical resistance value lowers at the time the leading coil element of the composite coil is pushed out of the opening of the catheter body, while the electrical resistance value rises at the time the joint member is situated at the opening of the catheter body is repeated.

At the time the third rise in electrical resistance value was monitored and its value reached the maximum, a high-frequency current of 0.5 W was applied through the terminal. At this time, by radiography, the third joint member from the leading side was observed being severed. When the wire device was then pulled back, 2 coil elements were easily recovered with their original forms retained.

As apparent from the above results, according to the medical implements according to the present invention, the length or volume of an implanted device portion actually separated and deposited can be changed or adjusted by selecting a joint member to be severed in a state that the wire device has been inserted, because the implanted device in the wire device for depositing the implanted device has plural severable joints including a joint between the implanted device and the wire for deposition. Accordingly, an implanted device of an extremely appropriate length or volume can be deposited and left even when conditions of an actual deposition site are against expectation.

EFFECTS OF THE INVENTION

According to the medical implements of the present invention for depositing an implanted device, the length or volume of an implanted device portion actually deposited can be changed or adjusted even in a state that the wire device has been inserted. Accordingly, an implanted device of an appropriate length or volume can be deposited and left.

As a result, according to the present invention, it takes only an extremely short time to deposit the implanted device, and so mental and physical burdens imposed on doctors and patients can be lightened to a great extent. In addition, its operation is easy, and high reliability can be obtained.

We claim:

1. A medical implement for depositing an implanted device comprising a catheter which is to be inserted into a patient's body and has an electrode at a distal part of said catheter, and a wire device for depositing the implanted device, which is guided by the catheter, wherein the wire device comprises a wire for depositing the implanted device, and the implanted device connected being to a distal end of the wire through a first severable joint member, said implanted device having a structure such that a plurality of implanted elements are joined to each other through one or more second severable joint members successively, and wherein the first joint member or any one of the second joint members of the wire device is severed by supplying the electrode of the catheter with electric power in a state such that the implanted device of the wire device guided through the catheter is projected from the distal end of the catheter.

2. The medical implement according to claim 1 for depositing an implanted device, wherein the first joint member or any one of the second joint members is melted and severed at the distal end of the catheter by applying a high-frequency current to the electrode of the catheter.

3. The medical implement according to claim 1 or 2 for depositing an implanted device, wherein the implanted elements of the implanted device are formed by a biocompatible metallic coil.

4. The medical implement according to claim 1 for depositing an implanted device, wherein the first joint member and the second joint members are formed by a material capable of being melted and severed by heat.

5. The medical implement according to claim 4 for depositing an implanted device, wherein a material for the first joint member and the second joint members is a polyvinyl alcohol type polymer.

6. The medical implement according to claim 1 for depositing an implanted device, wherein a leading implanted element among the plurality of implanted elements making up of the implanted device is the longest implanted element.

7. The medical implement according to claim 1 for depositing an implanted device, wherein the first joint member and the second joint member or plural second joint members are formed by an integral common joint member.

8. The medical implement according to claim 1 for depositing an implanted device, wherein the implanted elements are provided with a fibrous material for promoting the formation of thrombus.

9. The medical implement according to claim 1 for depositing an implanted device, wherein the implanted elements have a shape-memory property.

10. The medical implement according to claim 2, for depositing an implanted device, wherein the implanted elements of the implanted device are formed by a biocompatible metallic coil.

11. A method of depositing an implanted device, which comprises the steps of:

inserting a catheter having an electrode at its distal part into a patient's body to locate the distal part at a site intended to deposit the implanted device; and guiding a wire device for depositing the implanted device, which wire device comprises a wire for depositing the implanted device, and the implanted device being connected to the distal end of the wire through a first severable joint member, said implanted device having a structure such that a plurality of implanted elements are joined to each other through one or more second severable joint members successively, through the catheter to sever the first joint member or any one of the second joint members of the wire device by supplying the electrode of the catheter with electric power in a state such that the implanted device is projected from the distal end of the catheter, whereby the whole or a part of the implanted elements is deposited at the intended site.

12. The method of depositing an implanted device according to claim 10, wherein the step of severing the first joint member or any one of the second joint members is conducted by applying a monopolar high-frequency current between the electrode of the catheter and a counter electrode for body ground provided on the skin surface of the patient's body.

* * * * *